United States Patent
Didier

Patent Number: 5,556,544
Date of Patent: Sep. 17, 1996

[54] CONCENTRATOR & FILTER

[76] Inventor: Emmanuel R. Didier, 111 Marquez Pl., Pacific Palisades, Calif. 90272

[21] Appl. No.: 525,182

[22] Filed: Sep. 8, 1995

[51] Int. Cl.⁶ .................................................. B01D 35/28
[52] U.S. Cl. .......................... 210/436; 210/446; 210/453; 210/455; 210/472; 210/474; 209/172; 209/173; 422/99; 422/100; 422/101
[58] Field of Search .................................. 209/3, 172, 17, 209/173; 210/436, 446, 453, 455, 464, 472, 474; 422/99, 101, 102

[56] References Cited

U.S. PATENT DOCUMENTS

| | | |
|---|---|---|
| 3,800,945 | 4/1974 | Smith . |
| 4,081,356 | 3/1978 | Zierdt . |
| 4,246,123 | 1/1981 | Cornell et al. . |
| 4,439,319 | 3/1984 | Rock . |
| 4,555,336 | 11/1985 | Nugent et al. . |
| 4,675,110 | 6/1987 | Fay . |
| 4,683,058 | 7/1987 | Lyman et al. . |
| 4,722,792 | 2/1988 | Miyagi et al. . |
| 4,769,145 | 9/1988 | Nakajima . |
| 4,824,560 | 4/1989 | Alspector . |
| 4,832,851 | 5/1989 | Bowers et al. . |
| 4,956,103 | 9/1990 | Jessop et al. . |
| 5,104,533 | 4/1992 | Szabados . |
| 5,108,381 | 4/1992 | Kolozsi . |
| 5,208,161 | 5/1993 | Saunders et al. . |
| 5,244,635 | 9/1993 | Rabson et al. . |
| 5,252,460 | 10/1993 | Fiedler et al. . |
| 5,254,314 | 10/1993 | Yu et al. . |
| 5,256,314 | 10/1993 | Driessen . |
| 5,277,873 | 1/1994 | Hsei . |
| 5,283,038 | 2/1994 | Seymour . |
| 5,308,483 | 5/1994 | Sklar et al. . |
| 5,316,732 | 5/1994 | Golukov et al. . |
| 5,318,748 | 6/1994 | Babson et al. . |
| 5,330,916 | 7/1994 | Williams et al. . |
| 5,356,814 | 10/1994 | Carrico, Jr. et al. . |

Primary Examiner—David A. Reifsnyder

[57] ABSTRACT

A fecal parasite concentrator which has a cylindrical body (20) with connections for a sample vial (24) on one end and a centrifuge tube (28) on the other. An integral filter (36) is disposed within the body at right angles coaxially covering the cross sectional area of the hollow body. The filter contains a series of closely spaced square openings for filtration of a liquid diluted fecal specimen. A hollow stem (40) with truncated end (44) extends upwardly from the filter and a number of geometrically shaped orifices (46) permit air to pass therethrough when the diluant specimen flows through the filter.

13 Claims, 2 Drawing Sheets

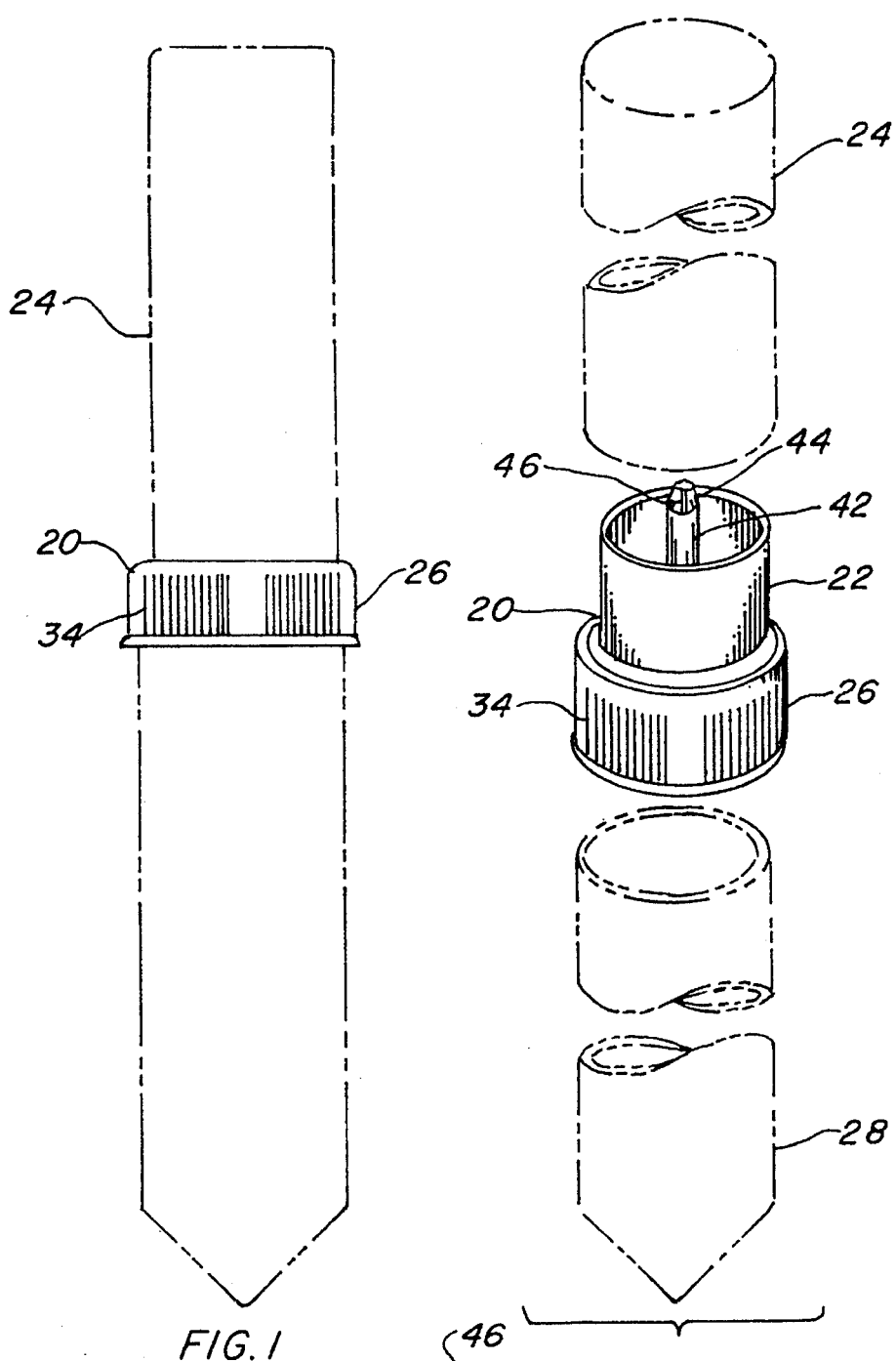

CONCENTRATOR & FILTER

TECHNICAL FIELD

The invention relates in general, to filters for processing fecal samples to separate parasite eggs and larvae. More specifically, the invention pertains to a filter having connections for a sample vial and a centrifuge tube including a hollow stem for equalizing pressure therebetween.

BACKGROUND ART

Previously, many types of filters have been used in endeavoring to provide an effective means for the separation of parasite eggs and larvae from feces samples. Over the years, many types of devices have been developed to concentrate parasitic eggs and larvae also protozoan cysts and to recover coccidian occysts such as isospora belli and cryptosporidium parvium.

A search of the prior art did not disclose any patents that read directly on the claims of the instant invention, however the following U.S. patents are considered related:

| PATENT NO. | INVENTOR | ISSUED |
|---|---|---|
| 4,081,356 | Zierdt | 23 March 1978 |
| 4,675,110 | Fay | 23 June 1987 |

The U.S. Pat. No. 4,081,356 Zierdt discloses a current device and method for recovering parasitic eggs and larvae from feces samples. In this device, a cup is attached to an open ended tube forming an emulsification chamber. A filter is attached to the chamber which includes a coaxial tube for the passage of air and a centrifuge tube is attached by an annular collar to form a separating chamber. Zierdt also teaches a method which includes: the adding of liquids to dilute the sample, mechanical stirring, shaking and straining to separate the sediment containing eggs and larvae, and decanting the supernatant fluid after centrifuging. This process utilizes a separate filter using a metal or plastic 30 mesh screen. The gas passage tube, which has a 0.1 inch outside diameter and a 0.06 inside diameter is located in the center of the filter and leaves much to be desired as it is easily clogged and blocked by debris. Further, the double ended cap is expensive and unnecessarily complicated.

The U.S. Pat. No. 4,675,110 Fay discloses a device and method for the concentration of parasite eggs and larvae. The device consists of separable upper and lower chambers connected by a mid-piece which incorporates a filter of stainless steel gauze. The sample is emulsified in the upper chamber and is filtered into the lower chamber. Ether is added to the upper chamber, and the mid-piece and upper chamber are removed. The lower chamber is then shaken and centrifuged, the mid-plug of debris is removed, and the tube is drained and swabbed clean leaving a small sediment containing the sediment containing the parasite eggs and larvae. The sediment is removed by extraction with Lugol's iodine or saline to dilute the sediment. The filter used in this device is relatively complex and expensive. Also, the Fay device utilizes a number of gas return passages which are arranged around the exterior of the filter insert and which create multiple apertures. These apertures, function to equalize pressure between the chambers however, it nonetheless requires frequent agitation to clear the passage of undigested vegetable matter and other debris. Further, separate tooling is required for each piece obviously affecting the overall cost of the device which is disposed of after use.

Other systems and methods have been utilized for the same purpose such as the fecal parasite, concentrator known by its registered trademark FPC and JUMBO and manufactured by Evergreen Scientific of Los Angeles, Calif. The JUMBO concentrator functions in the same manner as described above and connects a vial and tube together as with Fay's teachings. A movable vent-straw is located in the center of the strainer unit and requires manually pulling the straw out approximately 1.0 inch (2.54 cm) prior to attachment of the specimen vial. The problems of clogging and blocking the pressure equalizing element still exist and multiple components are employed.

For background purposes and as indicative of the art to which the invention relates reference may be made to the remaining cited patents.

| PATENT NO. | INVENTOR | ISSUED |
|---|---|---|
| 4,439,319 | Rock | 27 March 1984 |
| 4,555,336 | Nugent et al | 26 November 1985 |
| 4,722,792 | Miyagi et al | 2 February 1988 |
| 4,769,145 | Nakajima | 6 September 1988 |
| 4,824,560 | Alspector | 25 April 1989 |
| 4,832,851 | Bowers et al | 23 May 1989 |
| 4,956,103 | Jessop et al | 11 September 1990 |
| 5,108,381 | Kolozsi | 28 April 1992 |
| 5,208,161 | Saunders et al | 4 May 1993 |
| 5,244,635 | Rabson et al | 14 September 1993 |
| 5,252,460 | Fiedler et al | 12 October 1993 |
| 5,254,314 | Yu et al | 19 October 1993 |
| 5,256,314 | Driessen | 26 October 1993 |
| 5,277,873 | Hsei | 11 January 1994 |
| 5,283,038 | Seymour | 1 February 1994 |
| 5,308,483 | Sklar et al | 3 May 1994 |
| 5,316,732 | Golukhov et al | 31 May 1994 |
| 5,318,748 | Babson et al | 7 June 1994 |
| 5,330,916 | Williams et al | 19 July 1994 |
| 5,356,814 | Carrico, Jr. et al | 18 October 1994 |

DISCLOSURE OF THE INVENTION

While much effort has been applied in the field for this specific method of separating fecal test samples, there is still room for improvement. The simplicity of using standard well known and readably available vials and tubes has been accepted by prior art in general. However, many approaches to solving the problem of the pressure equalizer from one side of the filter screen to the other is still remains unresolved as a myriad of approaches have been tried and no common conclusion has been reached.

It is therefore a primary object of the invention to provide an equalizing device that resists clogging and blocking while permitting air to pass through the device. Thus, allowing the vapor pressure to balance on each side of the filter screen quickly with a minimum amount of agitation required. This object is achieved using a hollow stem in the center of the filter that has a tapered inside diameter and that extends partially into the sample vial.

Further, the stem is truncated and contains four geometrically shaped orifices that are positioned strategically and have proven to be functionally effective. The combination of the level of the fluid relative to the orifice position, allows air to pass through easily while the filtration level is more than sufficient to accomplish the desired results.

An important object of the invention is the simplicity of manufacture, as the entire device including the connecting means, filter and hollow stem are formed of a single, integral molded part. Hermetic seals are easily achieved with the vial and tube and no other parts are necessary to handle or manipulate.

Another object of the invention is directed to the minimal cost of the device as it is fabricated by an injection molded process. This process requires only an initial cost for the tooling after which, multiple units may then be rapidly and inexpensively produced.

Still another object of the invention is its ease of understanding and use. Since only one single part is required to be used in combination with well known vials and tubes, the actual mechanics are easily understood and used by any knowledgeable technician.

Yet another object of the invention is directed to the large filter area available for filtration. Prior art that includes orifices and passageways on the periphery use large areas for air equalization whereas the instant invention employs only a hollow stem in the center allowing the balance of the area to function as a filtering surface.

A further object of the invention is the positive seal created by an interference fit for the vial and a threaded joint for the tube. Both of these sealing methods create a positive hermetic closure which eliminates leakage that would invalidate the sample.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is an elevational view of the preferred embodiment with a sample vial and centrifuge tube shown in phantom.

FIG. 2 is an exploded view of the preferred embodiment with the vial and tube shown in phantom as above.

FIG. 3 is a plan view of the preferred embodiment.

FIG. 4 is an elevation view of the preferred embodiment.

FIG. 5 is a bottom view of the preferred embodiment.

BEST MODE FOR CARRYING OUT THE INVENTION

Figure 6:
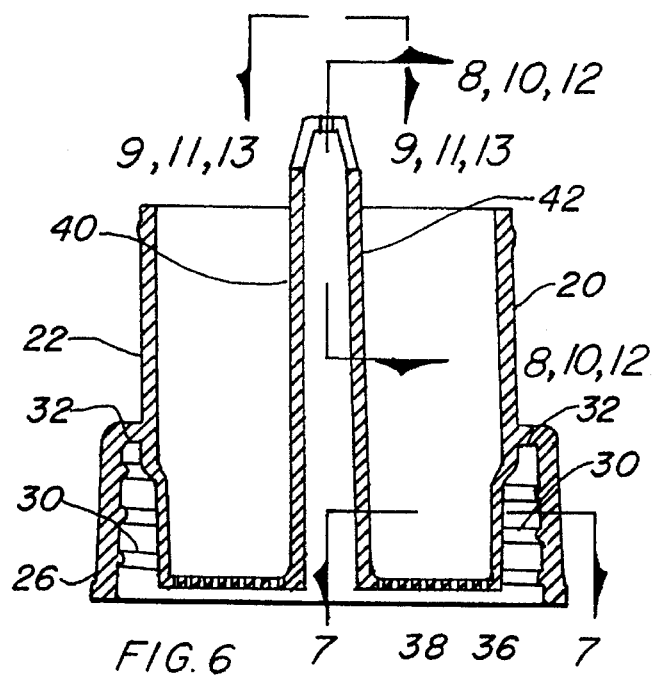
FIG. 6 is an enlarged cross sectional view of the preferred embodiment taken along the vertical centerline of the device.

The best mode for carrying out the invention is presented in terms of a preferred embodiment with a second and third embodiment of the orifice shape in the stem truncated end.

The preferred embodiment as shown in FIGS. 1 through 9 is comprised of the following major elements: a cylindrical body 20, a sample vial 24, a centrifuge tube 28, an integral filter 36, a hollow stem 40 and orifices 46. The cylindrical body 20 is basically hollow and is made of a thermoplastic material such as polyethylene, polystyrene, polycarbonate or the like with polypropylene preferred. The body 20 has sample vial connecting means integral with a first end 22 for fastening the conventional sample vial 24. The fastening is accomplished using an interference fit where the vial is simply forced over the outside diameter of the body first end 22. This type of fit for vials of this type is well known in the art and produces a liquid tight seal. The preferred sample vial 24 utilized is the 30 milliliter size which is in common usage and readily available in the medical field.

The body 20 further contains centrifuge tube connecting means integral with a second end 26 for fastening the conventional centrifuge tube 28. The fastening accomplished using male threads 30 that grip female threads, normally included in the centrifuge tube 28. The body 20 further contains an inwardly depending lip 32 that is located inward of the male threads 30 creating a sealing barrier between the tube 28 and the body 20 permitting a liquid tight seal to be made when the tube 28 is rotatably tightened into the body 20. The threaded portion of the body 20 fits over the tube 28 much like a cap as a matter of fact, the connection means has the appearance of a cap including a series of finger gripping grooves 34 located peripherically around the connecting means. These grooves 34 provide a gripping surface for ease of manually rotating the body 20 on the threaded centrifuge tube 28.

Figure 7:
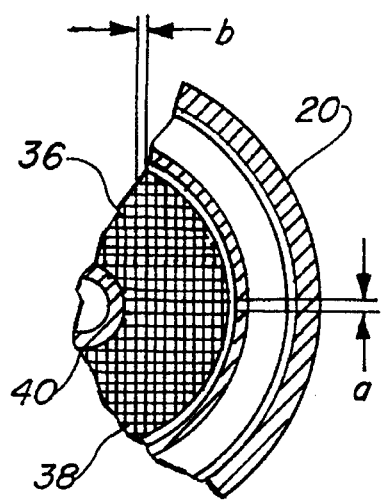
FIG. 7 is a cross sectional view taken along lines 7—7 of FIG. 6 with the openings in the filter designated "a" for height and "b" for width.
Figure 8:
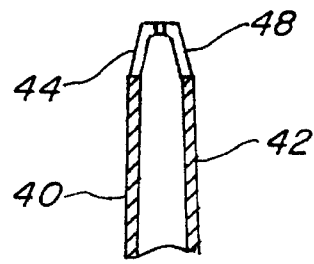
FIG. 8 is a cross sectional view taken along lines 8—8 of FIG. 6 illustrating partially the cross section of the stem in the preferred embodiment.
Figure 9:
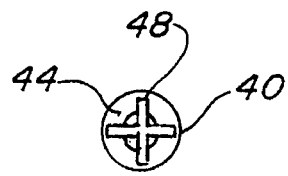
FIG. 9 is a cross sectional view taken along lines 9—9 of FIG. 6 illustrating partially the top of the stem in the preferred embodiment.

The integral filter 36 extends into the centrifuge tube connecting means and is at right angles to the body 20, coaxially covering the entire cross sectional area of the cylindrical body. The filter 36 divides the internal space within the body between the vial 24 and tube 28 and is used to strain and retain access fecal debris such as undigested vegetable matter from the liquid diluent specimen that is contained within the sample vial 24. Thus, allowing only small particles in solution to pass into the tube 28 along with its liquid diluent. The filter 36 is integrally formed with the body 20 and contains a multiplicity of perforated square openings 38 molded completely through. The openings 38 are from 0.5 millimeters to 0.7 millimeters in height and in width with 0.6 millimeters being preferred. FIG. 7 illustrates the filter in an enlarged view with the openings designated "a" for height and "b" for width which are obviously equal and represent the size limitations noted.

The hollow stem 40 is located in the center of the filter 36 and extends upward away from the filter surface so that a centrally upstanding hollow stem is provided. The stem 40 is parallel with the body first end 22 and functions to equalize the pressure between the vial 24 and the tube 28 when the liquid diluted fecal specimen is strained and flows therebetween.

The hollow stem 40 is best illustrated in the cross section of FIG. 6 and has an inwardly tapered shank 42 with an inside diameter of from 0.38 millimeter to 0.42 millimeters at the filter abutment end with 0.40 millimeters preferred. The upstanding end of the shank 42 has an inside diameter of from 0.30 millimeters to 0,34 millimeters with 0.32 millimeters being found to be ideal. The taper of the steam has a distinct bearing on its ability to equalize the pressure and has proven successful in the preferred relationship.

The hollow stem 40 terminates with a truncated end 44 that protrudes above the body first end 22 preferably 0.64 millimeters which is sufficient to properly equalize pressure relative to the liquid level. The truncated end 46 further contains a number of geometrically shaped orifices 46 for air passage with the quality of four orifices bring favored.

There are three embodiments of the orifices 46 all of which are geometrical in shape and the same number, positioned concentrically.

The preferred embodiment is illustrated in FIGS. 3–5, 8 and 9 and consists of interceding rectangular slots 48 forming a cross shape, two in each plane terminating at four places 90 degrees apart.

Figure 10:
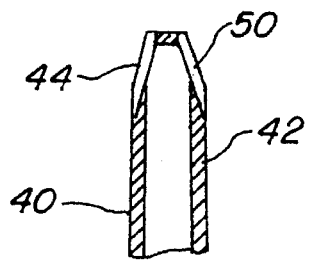
FIG. 10 is a cross sectional view taken along lines 10—10 of FIG. 6 illustrating partially the cross section of the stem in the second embodiment.
Figure 11:
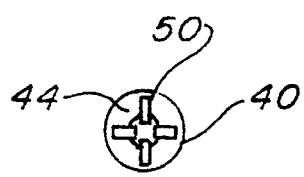
FIG. 11 is a cross sectional view taken along lines 11—11 of FIG. 6 illustrating partially the top of the stem in the second embodiment.

The second embodiment is depicted in FIGS. 10 and 11 and utilize four diagonally tapered slots 50 positioned at right angles to each other within the truncated end 44 tapered portion. This leaves the apex or top intact with no openings protruding directly through.

Figure 12:
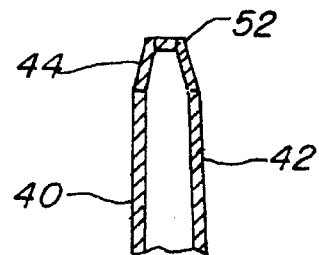
FIG. 12 is a cross sectional view taken along lines 12—12 of FIG. 6 illustrating partially the cross section of the stem in the third embodiment.
Figure 13:
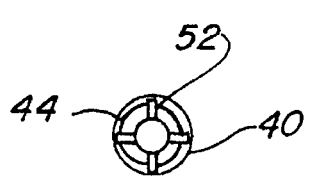
FIG. 13 is a cross sectional view taken along lines 13—13 of FIG. 6 illustrating partially the top of the stem in the third or preferred embodiment.

The third embodiment of the orifice 46 is shown in FIGS. 12 and 13 and employs four equally spaced right angular circular sectors 52 within the truncated end 44 tapered portion again the apex of the truncation is intact with no feed through at this point.

It may be readily seen that the three embodiments function in the same manner and only the geometry of the openings differ therefore, other configurations and combinations may also be used with ease.

In function, the fecal parasite concentrator may use the commonly accepted Ritchie formula-ether method or Zierdt's method as described in the BACKGROUND ART discussion of U.S. Pat. No. 4,081,365. Any other modified or diverse methods may also be employed as long as they require the closed two tube system and filtration of a diluent with the sample in a liquid solution is required.

While the invention has been described in complete detail and pictorially shown in the accompanying drawings it is not to be limited to such details, since many changes and modifications may be made in the invention without departing from the spirit and scope thereof. Hence, it is described to cover any and all modifications and forms which may come within the language and scope of the appended claims.

I claim:

1. A fecal parasite concentrator filter comprising:
    (a) a cylindrical body having a first end and a second end,
    (b) sample vial connection means integrally molded with the body first end for fastening a sample vial containing a liquid diluent fecal specimen,
    (c) centrifuge tube connection means integrally molded with the body second end for attaching a centrifuge tube thereupon,
    (d) a filter integrally molded with the body and extending into the centrifuge tube connecting means and terminating across the body at right angles for straining and retaining excess fecal debris from a liquid diluent specimen,
    (e) a hollow stem integrally molded with said filter, the hollow stem centrally upstanding and parallel with the body first end, the hollow stem abutting the filter at a filter abutment end being coterminous therewith, an upstanding end of the hollow stem at an opposite end to the filter abutment end, for equalizing pressure between the sample vial and the centrifuge tube connected to the body ends when liquid diluted fecal specimen flows therebetween, and
    (f) a truncated end inherent with the hollow stem having a plurality of orifices permitting air to pass therethrough while restricting solid matter.

2. The concentrator filter as recited in claim 1 wherein said body further comprises a thermoplastic material.

3. The concentrator filter as recited in claim 2 wherein said thermoplastic material further comprises polypropylene.

4. The concentrator filter as recited in claim 1 wherein said sample vial connection means further comprises an interference fit for sealing the first end of the body to a sample vial in a liquid tight manner.

5. The concentrator filter as recited in claim 1 wherein said centrifuge tube connection means further comprises a plurality of male threads that grippingly interface with female threads on a centrifuge tube and said body having an inwardly depending lip directly inward of the male threads creating a sealing barrier between the body and a centrifuge tube for a liquid tight interface.

6. The concentrator filter as recited in claim 1 wherein said centrifuge tube connecting means further having a plurality of finger gripping grooves peripherally located around the connecting means for ease of manually rotating the body upon the centrifuge tube.

7. The concentrator filter as recited in claim 1 wherein said filter having a multiplicity of perforated square openings from 0.5 millimeters to 0.7 millimeters.

8. The concentrator filter as recited in claim 1 wherein said hollow stem further comprises an inwardly tapered shank having an inside diameter of from 0.38 millimeters to 0.42 millimeters at the filter abutment end and 0.30 millimeters to 0.34 millimeters at the upstanding end.

9. The concentrator filter as recited in claim 1 wherein said truncated end protrudes above the body first end.

10. The concentrator filter as recited in claim 1 wherein said hollow stem truncated end orifices are interceding rectangular slots forming a cross shape.

11. The concentrator filter as recited in claim 1 wherein said hollow stem truncated end orifices are four diagonally tapered slots positioned at right angles to each other within the truncated end tapered portion.

12. The concentrator filter as recited in claim 1 wherein said hollow stem truncated end orifices are four equally spaced right angular circular sectors within the truncated end tapered portion, 13. The concentrator filter as recited in claim 1 wherein the plurality of orifices in the truncated end inherent with the hollow stem are geometrically shaped orifices.

* * * * *